(12) United States Patent
Roy et al.

(10) Patent No.: US 6,214,890 B1
(45) Date of Patent: Apr. 10, 2001

(54) FISCHER-TROPSCH SYNTHESIS PROCESS IN THE PRESENCE OF A CATALYST THE METALLIC PARTICLES OF WHICH HAVE A CONTROLLED SIZE

(75) Inventors: Magalie Roy; Blaise Didillon, both of Rueil Malmaison; Denis Uzio, Marly le Roi; Catherine Verdon, Rueil Malmaison, all of (FR)

(73) Assignee: Institut Francais Du Petrole, Rueil-Malmaison (FR)

( * ) Notice: Subject to any disclaimer, the term of this patent is extended or adjusted under 35 U.S.C. 154(b) by 0 days.

(21) Appl. No.: 09/373,229

(22) Filed: Aug. 12, 1999

(30) Foreign Application Priority Data

Aug. 12, 1998 (FR) .................................................. 98 10.346

(51) Int. Cl.⁷ ............................ C07C 27/00; B01J 23/00; B01J 23/40
(52) U.S. Cl. .......................... 518/715; 518/700; 502/325; 502/326
(58) Field of Search .................................. 518/715, 700; 502/325, 326

(56) References Cited

U.S. PATENT DOCUMENTS 5,756,419 * 5/1998 Chaumette et al. ................. 502/313

FOREIGN PATENT DOCUMENTS 0 581 619   2/1994   (EP) .
0 736 326   10/1996  (EP) .

* cited by examiner

Primary Examiner—Johann Richter
Assistant Examiner—J. Parsa
(74) Attorney, Agent, or Firm—Millen White Zelano & Branigan

(57) ABSTRACT

The invention relates to a synthesis process for hydrocarbons using a mixture containing carbon monoxide and hydrogen, called Fischer-Tropsch synthesis in the presence of a catalyst comprising a support, at least one group VIII metal said process being characterized in that at least 80% of the group VIII metallic particles of the catalyst have a size comprised between D–(D.0.2) and D+(D.0.2), where D represents the average size of the metallic particles. The process can be used in a fixed-bed reactor of the catalyst or in a reactor operating in liquid phase of the catalyst.

20 Claims, No Drawings

FISCHER-TROPSCH SYNTHESIS PROCESS IN THE PRESENCE OF A CATALYST THE METALLIC PARTICLES OF WHICH HAVE A CONTROLLED SIZE

The present invention relates to the field of catalysts used for the synthesis reactions of hydrocarbons starting from a mixture of gas containing carbon monoxide and hydrogen, generally called a Fischer-Topsch synthesis.

Therefore, the present invention relates to the use of a catalyst comprising at least one support and at least one group VIII metal in a synthesis process for hydrocarbons using a mixture containing carbon monoxide and hydrogen and optionally carbon dioxide denoted as CO—($CO_2$)—$H_2$.

DESCRIPTION OF THE PRIOR ART

The properties of the supported metallic catalysts, i.e. catalysts comprising one or more metals deposited on a support chosen from refractory oxides, carbon, polymers or any other material, are conditional upon a set of parameters, such as for example, the size of the metallic particles.

A large number of examples exist in the literature demonstrating the influence of the size of metallic crystallites on the activity of the final catalyst. This aspect has been described in extensive detail in "Catalysis by Metals and Alloys", V. Ponec, E. Bond, Study in Surface Science and Catalysis, Volume 95, page 280, 1995. On the other hand, the reduction in the size of these crystallites is often linked to an increase in the reaction between the metal and the support.

The catalysts used for the conversion of synthesis gas into hydrocarbons, operated at high temperature and under pressure (known in the literature under the name Fischer-Tropsch synthesis) require specific crystallites size conditions.

Thus the group VIII metals of the periodic classification of the elements, such as iron, ruthenium, cobalt, nickel catalyse the conversion of CO—($CO_2$)—$H_2$ mixtures (i.e. the CO—$H_2$ mixtures optionally containing $CO_2$, called synthesis gas) into liquid and/or gaseous hydrocarbons, For these reactions it is necessary to have catalysts the size of the metallic particles of which is controlled, i.e. the size of the particles and the distribution of particles as a function of the size is not random, in order to optimise the activity and the selectivity of the catalyst.

The conventional preparation methods for the supported metallic catalysts used for the Fischer-Tropsch synthesis consist of depositing a metallic salt or a metal-ligand coordination complex onto the support, then carrying out an activation stage consisting of one or more thermal treatments carried out under air or under hydrogen, which leads to a poor distribution of the size of the particles.

The Patent Application EP 0736326 A describes a new preparation method for a cobalt catalyst obtained by drying at a pressure lower than atmospheric pressure: the sizes of the cobalt particles obtained are comprised between 10 and 17 nm.

The Patent Application EP 0174696 A describes a preparation process for a cobalt-based Fischer-Tropsch catalyst where the cobalt is distributed such that $\Sigma Vp/\Sigma Vc<0.85$ ($\Sigma V$ being the quantity of Co contained in the periphery of the solid, $\Sigma Vc$ being the quantity of Co contained in the whole solid). The inventor shows that this distribution favours the formation of C5+. The catalyst is prepared by impregnation of the support (preferably silica) already immersed in water for 30 seconds, and can contain a promoter, preferably zirconium.

The U.S. Pat. No. 4,977,126 also describes a method of surface dispersion by vaporisation of a liquid in which the metallic compound is dissolved. A peripheral layer is thus formed.

Other U.S. Pat. No. 4,605,679 and U.S. Pat. No. 4,729,981 and the Patent Application EP 0535790A describe modifications to the reduction/activation stage.

However, the distribution in size of the group VIII metal particles and their interaction with the support are not very well controlled by these different techniques.

It is therefore advantageous, in order to increase the activity of the catalysts when using them in a hydrocarbons synthesis process, to have supported metallic catalysts for which the average size and their size distribution is controlled and the interactions with the supports limited, thanks to a new preparation method. In fact, it has been shown in the literature that the interaction between the metal or metals constituting the catalyst and the support used affect the reducibility and activity of the catalyst (cf. Z. Karpiniski, Adv. Catal. Vol. 37, p. 45, 1990).

This interaction between the metal and the support can be defined by a set of characterization techniques known to a person skilled in the art. For example, programmed thermoreduction which consists of determining the reduction temperature of the supported metal oxide can be mentioned. In fact it has been shown that the more the reduction temperature of the supported metal oxide is increased the more the interaction between the metal and the support is increased.

SUMMARY OF THE INVENTION

A new synthesis process for hydrocarbons using a mixture of synthesis gas containing carbon monoxide and hydrogen and optionally carbon dioxide in the presence of a catalyst comprising a support, at least one VIII group metal, i.e. groups 8, 9 and 10 of the new periodic classification (Handbook of Chemistry and Physics, $76^{th}$ edition, 1995–1996, on the inside front page) has been discovered and is the subject of the present invention, said process being characterised in that at least 80% of the group VIII metallic particles of the catalyst are of a size comprised between D−(D.0.2) and D+(D.0.2), where D represents the average size of the particles.

The metallic particles of the catalyst generally have an average size greater than 1 nm.

The process according to the invention is therefore carried out in the presence of a catalyst having an improved reducibility, i.e. the temperature necessary for the reduction of the catalyst is lower than the temperature necessary for the reduction of the catalyst according to the prior art. In fact the catalyst used in the synthesis process for hydrocarbons according to the invention has a reduction in the interaction between the group VIII metal and the support relative to the catalysts of the prior art, which allows an increase in the activity.

DETAILED DESCRIPTION OF THE INVENTION

The invention relates to the use of a catalyst in a synthesis process for hydrocarbons. The catalyst is characterized in that at least 80% of the particles of at least one group VIII metal have a size comprised between D−(D.0.2) and D+(D.0.2), where D represents the average size of the particles.

The catalyst is synthesized for example by the preparation of a colloidal suspension in aqueous phase, of at least one oxide of group VIII metal or metals to be supported, followed by the deposition of said suspension on a support, followed by the optional reduction of the oxide or oxides thus supported, In a preparation method for the catalyst used in the process according to the invention, the colloidal suspension of at least one metallic oxide of a group VIII metal is prepared in aqueous phase. With regard to other preparation methods for colloidal suspensions, this method uses water as a solvent, which has an advantage as regards safety, and leads to savings in terms of the cost of the process.

More particularly, the preparation method for the catalyst used in the process according to the present invention includes several stages:

a) preparation of a colloidal suspension of at least one metallic oxide, in aqueous phase, b) deposition of the colloidal suspension by impregnation on a support, c) drying at a temperature less than or equal to 250° C.

d) optional calcination at a temperature ranging up to 700° C.

e) optional reduction

In stage a) the colloidal suspension is obtained for example by hydrolysis of at least one metallic cation of at least one group VIII metal in an aqueous medium, which leads to the formation of oxide or hydroxide particles in suspension.

Preferably, the hydrolysis can be carried out for example by neutralization of an aqueous solution containing a precursor salt of a group VIII metal capable of leading to the metallic hydroxide or metallic oxide, the neutralization can be carried out using at least one mineral base such as for example soda, potash or an ammonium hydroxide solution.

The group VIII metal is preferably chosen from cobalt, iron, ruthenium and nickel, and more preferably cobalt.

The group VIII metal salts which can be used in the preparation method according to the invention are preferably nitrates, or any other salt capable of generating a precursor of a group VIII metal in solution and leading to hydroxides or oxides which give rise to the formation of particles in suspension.

The solution containing the mineral base used for the neutralization can be poured for example into the aqueous solution containing a metallic salt or salts or, inversely, the solution containing the metallic salt or salts can be poured into the solution containing the mineral base. The colloidal suspension can also be prepared by at least partially pouring the two solutions simultaneously into the apparatus used to prepare the colloidal suspension.

During the preparation of the colloidal suspension of metallic oxides, one or more other metallic salts can be optionally introduced at any time during the preparation. This salt or these salts can optionally lead to the formation of oxide(s) or hydroxide(s) in an aqueous medium or not be converted in the reaction medium. These additional metals are preferably ruthenium, tantalum and molybdenum.

The compounds aiming to stabilize the colloidal suspension can be introduced during the preparation of the colloidal suspension. Among these compounds, hydrogen protons, nitrites and ethylenediamine protons can for example be mentioned this list not being limitative.

After hydrolysis carried out by neutralization of at least one part of the solution containing the group VIII metal salts, it is optionally possible to leave the colloidal suspension under agitation, optionally after modification of the pH by adding quantities of acid or base compatible with the stability of the colloidal suspension.

In the case where the catalyst must be cleared of most of the alkali or alkaline-earth metals which it can contain, it is possible to eliminate most of these said metals by adding an aqueous solution with adjusted pH to the colloidal suspension. The suspension or the precipitate obtained is then filtered and washed with an aqueous solution, then, if necessary, re-suspended in another aqueous solution, the pH and the composition of which are controlled in order to obtain a new colloidal suspension. This suspension can then be impregnated onto the support. These operations can optionally be carried out continuously, During the preparation of the colloidal suspension, monitoring of the operating parameters such as pH, the time for adding compounds forming the colloidal solution, the temperature, the duration of maturation, the addition of additives at different times during the preparation, the concentration of the medium or the ionic strength, allows the size of the oxide particles in the medium, their number and their aggregate state to be controlled.

In general, the preparation temperature is comprised between −10° C. and 100° C., preferably between 0° C. and 50° C., and very preferably between 0° C. and 35° C. The duration of maturation can generally vary between 0 and 40 hours, preferably between 15 minutes and 24 hours, and the ionic strength is preferably comprised between 0.005 and 20 moles per liter, more preferably between 0.01 and 10 moles per liter.

In stage b) the colloidal suspension containing the metal or metals in the form of oxide or hydroxide particles is then impregnated on a support. The support can be chosen from all the supports already described in the literature. At least one compound chosen from the refractory oxides can for example be used, such as silica, alumina, magnesia, silica-aluminas, aluminum silicates, carbons, and organic supports.

The support can optionally be subjected to a set of treatments before the impregnation stage such as calcination, hydration etc. The support can also already contain one or more metallic elements either introduced before impregnation of the colloidal suspension by conventional techniques, or introduced during the synthesis of the catalyst used in the process according to the invention.

Impregnation is preferably carried out under conditions such that the volume of the solution approximately corresponds to the pore volume of the support. Preferably the colloidal suspension is poured onto the support. This process can be carried out in a discontinuous manner, i.e. the preparation stage of the colloidal suspension precedes impregnation of said solution onto the support, or continuously, A process where hydrolysis of a solution containing at least one metallic salt is carried out by neutralization using at least one mineral base can be described as an example of a continuous process. For example the two solutions are poured simultaneously into a tank which, when full, overflows into an area containing the catalyst support.

After impregnation, the catalyst is preferably dried in stage c) at a temperature less than or equal to 250° C. in order to eliminate all or part of the water introduced during impregnation.

After drying, the catalyst can optionally be calcined in stage d) at a temperature ranging up to 700° C.

Then the catalyst can optionally be reduced in stage e). The reduction of the group VIII oxide metal is carried out using any reducing compound, for example molecular hydrogen or carbon monoxide or a mixture of the two. The reduction can take place either in-situ, i.e. in the reactor where the catalytic conversion is carried out, or ex-situ, i.e. in a different item of equipment from that where the catalytic reaction took place or partly in-situ and partly ex-situ. This pre-reduction can be carried out in gaseous phase or in a liquid phase containing at least one hydrocarbon having at least 5, preferably 10, carbon atoms per molecule if, subsequently the synthesis reaction for hydrocarbons takes place in a liquid phase containing at least one hydrocarbon having at least 5, preferably at least 10 carbon atoms per molecule.

The process according to the invention relates to the use of catalysts as described above in the production processes for a mixture of essentially linear and saturated hydrocarbons containing at least 25% by weight of C5+ hydrocarbons with regard to the group of hydrocarbons formed, using a synthesis gas.

The conditions for implementing the process for producing hydrocarbons according to the invention are usually as follows:

The conversion of the synthesis gas is operated under a total pressure comprised between 0.1 and 15 MPa, and preferably between 1 and 10 MPa, the temperature is generally comprised between 150 and 350° C., and preferably between 170 and 300° C.

The hourly space velocity is usually comprised between 100 and 20,000 volumes of synthesis gas per volume of catalyst and per hour and preferably between 400 and 10,000 volumes of synthesis gas per volume of catalyst and per hour, and the H2/CO ratio in the synthesis gas is usually comprised between 1:2 and 5:1; preferably between 1.2:1 and 2.5:1.

The process according to the invention can be implemented in any kind of reactor. A fixed-bed reactor or a reactor operating in liquid phase is preferably used such as a reactor in which the catalyst is in suspension in liquid phase (slurry) or such as a reactor operating in a trickling bed mode (trickle-bed reactor).

The following examples illustrate the invention without limiting its scope:

EXAMPLE 1

According to the Invention

Catalyst A is prepared by impregnation of a colloidal solution of cobalt oxide onto an alumina powder with a specific surface area equal to 180 m$^2$/g. The colloidal suspension is obtained by adding an ammonia solution (4 mol/l) to the cobalt nitrate solution (50 g/l) in order to obtain a pH=8.

The catalyst is dried at 120° C. and calcined at 250° C. The final cobalt content is 8%. The average size of the cobalt particles obtained using X-ray diffraction (XRD) is 15 nm. Microscopic analysis shows that according to the invention, more than 80% of the particles have a size comprised between 12.5 and 17.5 nm.

The TPR curve shows that the catalyst is totally reduced at a temperature less than 300° C. under a H$_2$/Ar mixture containing 5% hydrogen.

EXAMPLE 2

Comparative

Catalyst B is prepared using the same support as catalyst A by dry impregnation of a cobalt nitrate solution. The catalyst is dried at 120° C., then calcined at 400° C. so as to decompose the cobalt nitrate into oxide. The final cobalt content is 11.5%. The XRD analysis shows the presence of cobalt particles of a size comprised between 15 and 30 nm, the size of the particles being distributed in a random fashion.

The TPR curve shows that under a H$_2$/Ar mixture containing 5% hydrogen, it is necessary to raise the temperature to greater than 600° C. to completely reduce the cobalt oxide.

EXAMPLE 3

According to the Invention

Catalyst C is prepared by impregnation of a colloidal solution of cobalt oxide onto an alumina powder of specific surface area equal to 180 m$^2$/g. The colloidal suspension is obtained by adding a 0.75N potash solution to a cobalt nitrate solution (50 g/l) to obtain a pH equal to 7.5. The catalyst is then washed through a Büchner in order to remove the potassium ions. The catalyst is then dried at 120° C. and calcined at 250° C.

The final cobalt content is 6%. The XRD analysis shows the presence of cobalt particles of an average size equal to 10 nm. Microscopic analysis shows that according to the invention, more than 80% of particles have a size comprised between 8 and 12 nm. The TPR curve shows that the catalyst is totally reduced at a temperature of less than 300° C. under a mixture of H$_2$/Ar containing 5% hydrogen.

EXAMPLE 4

Evaluation of the Performances of Catalysts A, B, C

Catalysts A, B, C the preparations of which are described in the examples above were tested in the conversion reaction for synthesis gas (CO—H$_2$). The reaction took place in a fixed bed in gaseous phase in a unit operated continuously on 20 cm$^3$ of catalyst. The catalysts are reduced beforehand "in situ" under pure hydrogen at atmospheric pressure, at 250° C. for the catalysts according to the invention, at 350° C. for catalyst B. The test conditions are as follows:

T=220° C.

P=2 MPa hourly space velocity (by volume): HSV=1500 h$^{-1}$ molar ratio H$_2$/CO=2

The results are as follows:

| Catalyst | % Co (weight %) | CO conversion (%) (per g of Co) | Distribution of the products formed (weight %) | | |
|---|---|---|---|---|---|
| | | | C1 | C1–C4 | C5+ |
| A | 8 | 28 | 10 | 22 | 78 |
| B | 12 | 25 | 13 | 22.5 | 74.5 |
| C | 6 | 20 | 12 | 23 | 77 |

These results show that the use of catalysts in a synthesis gas conversion process allows a gain as regards the reduction temperature necessary for reducing the cobalt oxides to cobalt of at least 100° C. relative to the process in the presence of a catalyst according to the prior art, whilst having catalytic performances as good as or even better than the processes of the prior art.

What is claimed is:

1. A process for the synthesis of hydrocarbons using a mixture containing carbon monoxide and hydrogen in the presence of a catalyst comprising a support and catalytically active metallic components consisting of at least one group VIII metal, said process being characterized in that at least 80% of the group VIII metallic particles of the catalyst have a size comprised between D−(D.0.2) and D+(D.0.2), where D represents the average size of the metallic particles.

2. A process according to claim 1 wherein the mixture further contains carbon dioxide.

3. A process according to claim 1 wherein the catalyst is prepared according to the following steps a) preparation of a colloidal suspension of at least one group VIII metallic oxide in aqueous phase b) deposition of the colloidal suspension by impregnation onto a support, and c) drying at a temperature lower than or equal to 250° C.

4. A process according to claim 3, wherein the catalyst is prepared using a colloidal suspension obtained by the hydrolysis of at least one metallic cation of at least one group VIII metal in aqueous medium.

5. A process according to claim 4 wherein hydrolysis is carried out using at least one mineral base.

6. A process according to claim 5 wherein the mineral base is a soda, potash, or ammonia solution.

7. A process according to claim 1 wherein the group VIII metal of the catalyst is cobalt, iron, ruthenium or nickel.

8. A process according to claim 7 wherein the group VIII metal is cobalt.

9. A process according to claim 3, wherein a metal salt of ruthenium, added to the colloidal suspension.

10. A process according to claim 3, wherein the catalyst is prepared at a temperature comprised between −10° C. and 100° C., for a duration of maturation comprised between 0 and 40 hours, and with an ionic strength comprised between 0.005 and 20 moles per liter.

11. A process according to claim 3, further comprising reducing the catalyst.

12. A process according to claim 1 operated under a total pressure comprised between 0.1 and 15 MPa, at a temperature comprised between 150 and 350° C. with a hourly volume velocity comprised between 100 and 20,000 volumes of synthesis gas per volume of catalyst and per hour, the H2/CO ratio in the synthesis gas being comprised between 1:2 and 5:1.

13. A process according to claim 1 operated in a catalyst fixed-bed reactor.

14. A process according to claim 1 operated in a reactor working in liquid phase in which the catalyst is in suspension in the liquid phase.

15. A process for the synthesis of hydrocarbons using a mixture containing carbon monoxide and hydrogen in the presence of a catalyst comprising a support and catalytically active metallic components consisting of tantalum and at least one group VIII metal, said process being characterized in that at least 80% of the group VIII metallic particles of the catalyst have a size comprised between D−(D.0.2) and D+(D.0.2), where D represents the average size of the metallic particles.

16. A process for the synthesis of hydrocarbons using a mixture containing carbon monoxide and hydrogen in the presence of a catalyst comprising a support and at least one group VIII metal, said process comprising preparing the catalyst by:

a) preparation of a colloidal suspension of at least one group VIII metallic oxide in aqueous phase b) deposition of the colloidal suspension by impregnation onto a support, and c) drying at a temperature lower than or equal to 250° C., and monitoring at least one process parameter in order to control particle size and state of aggregation of the group VIII metallic particles so that at least 80% of the group VIII metallic particles of the catalyst have a size comprised between D−(D.0.2) and D+(D.0.2), where D represents the average size of the metallic particles.

17. A process according to claim 16, wherein said at least one process parameter comprises pH, time for adding compounds forming the colloidal suspension, temperature, duration of maturation, addition of additives at different times during preparation, concentration of the medium or ionic strength of the medium.

18. A process according to claim 17, wherein the catalyst is prepared using a colloidal suspension obtained by the hydrolysis of at least one metallic cation of at least one group VIII metal in aqueous medium.

19. A process according to claim 18, wherein said aqueous solution is an ammoniacal solution.

20. A process according to claim 19, wherein the group VIII metal is cobalt.

* * * * *

UNITED STATES PATENT AND TRADEMARK OFFICE
CERTIFICATE OF CORRECTION

PATENT NO. : 6,214,890 B1
DATED : April 10, 2001
INVENTOR(S) : Roy et al.

It is certified that error appears in the above-identified patent and that said Letters Patent is hereby corrected as shown below:

Column 7,
Line 44, change "catalyst" to -- catalytic --.

Signed and Sealed this

Twenty-sixth Day of February, 2002

Attest:

JAMES E. ROGAN
Attesting Officer    Director of the United States Patent and Trademark Office